United States Patent [19]
Phillips

[11] Patent Number: 5,431,913
[45] Date of Patent: Jul. 11, 1995

[54] SKIN CLEANSING AND EXFOLIANT COMPOSITION AND METHOD OF TREATING SKIN

[76] Inventor: Eva J. Phillips, 2810 Thousand Oaks Dr. #239, San Antonio, Tex. 78232

[21] Appl. No.: 181,498

[22] Filed: Jan. 14, 1994

Related U.S. Application Data

[63] Continuation-in-part of Ser. No. 51,795, Apr. 26, 1993, abandoned, which is a continuation of Ser. No. 825,252, Jan. 24, 1992, abandoned.

[51] Int. Cl.$^6$ ............................ A61K 9/10; A61K 7/50
[52] U.S. Cl. ................................. 424/401; 514/725; 514/844; 514/846; 514/937; 514/859
[58] Field of Search ............... 424/401; 514/844, 846, 514/725, 937, 859

[56] References Cited

U.S. PATENT DOCUMENTS

| | | | |
|---|---|---|---|
| 4,532,133 | 7/1985 | Schmidt | 514/725 |
| 4,608,392 | 8/1986 | Jacquet et al. | 514/844 |
| 4,707,354 | 11/1987 | Garlen et al. | 424/47 |
| 4,826,828 | 5/1989 | Wilmott et al. | 514/63 |
| 4,839,164 | 7/1989 | Smith | 424/64 |
| 4,888,363 | 12/1989 | Dulak et al. | 514/725 |
| 4,981,845 | 1/1991 | Pereira | 514/557 |
| 4,992,265 | 2/1991 | Davis et al. | 424/70 |
| 5,093,360 | 3/1992 | Yu et al. | 514/725 |
| 5,153,230 | 10/1992 | Jaffery | 514/847 |
| 5,252,604 | 10/1993 | Nagy | 514/859 |
| 5,380,764 | 1/1995 | Herzog | 514/725 |

*Primary Examiner*—Thurman K. Page
*Assistant Examiner*—Amy Hulina
*Attorney, Agent, or Firm*—Hill, Steadman & Simpson

[57] ABSTRACT

A skin cleansing and exfoliant composition comprising d-alpha tocopheryl acetate (Vitamin E) homogenized in a pharmacologically acceptable oil phase and an emulsion or suspension of retinoic acid or a pharmacologically acceptable derivative thereof in a pharmacologically acceptable fluid adapted for application to human or non-human animal skin, the portion of oil phase being sufficient to provide a concentration of oil phase in the emulsion or suspension of from about 20% to about 40% by weight and the portion of retinoic acid or derivative thereof being sufficient to provide a concentration in the emulsion or suspension of from about 60% to about 80% by weight. A method for using the composition is also disclosed.

12 Claims, No Drawings

SKIN CLEANSING AND EXFOLIANT COMPOSITION AND METHOD OF TREATING SKIN

RELATED APPLICATIONS

This is a continuation-in-part of application Ser. No. 08/051,795 filed Apr. 26, 1993, abandoned which is a continuation of application Ser. No. 07/825,252 filed Jan. 24, 1992, abandoned.

BACKGROUND OF THE INVENTION

1. Field of the Invention

The present invention relates to skin cleansing and exfoliant compositions and methods of treating skin.

2. Discussion of the Prior Art

The skin of the human body and, more specifically, facial skin, as well as the skin of certain non-human animals, periodically needs a deep cleansing to remove not only the oily particles resulting from secretions, but also dead skin caused by desquamation of the epidermis.

An exfoliant cleansing or "peeling" promotes the partial regeneration of epidermal tissues, restoring the skin's freshness and suppleness and favoring the application and the penetration of cosmetics or dermo-pharmaceutical products.

The cleansing of the skin can be achieved utilizing detergent solutions, but these have a tendency to cause pronounced drying of the skin without completely removing foreign matter.

There have also been proposed to effect the exfoliation of the epidermis compositions in the form of creams containing abrasive substances comprised of insoluble particles in the appropriate size and shape such as, for example, quartz particles which, after application to the parts of the body to be cleansed, are removed by wiping or rinsing with water. Such compositions are particularly effective but may be highly irritating. In addition, particles of the abrasive materials can remain in the pores of the skin and thus cannot be totally removed.

More recently, aqueous compositions in the form of creams which contain abrasives in the form of mineral substances or sugars with low hydrosolubility in the cream, but which can dissolve during the cleansing of the skin with water, have been proposed. Since the purpose of these compositions is to eliminate oily substances, these products are generally devoid of such products, but when they do contain them, they are present in a proportion less than about 5% by weight.

Since the abrasive particles have low hydrosolubility, their removal during rinsing with water is often slow and incomplete.

Moreover, by drying on the skin, the compositions present the inconvenience of not allowing a prolonged massage which is necessary to obtain proper exfoliant action.

It has been suggested to use cleansing compositions which leave the skin fresh and clean, totally free from oils, dirt and dead skin, by applying an anhydrous composition to the skin and massaging; this composition containing, in an oily phase, an emulsifying agent and highly hydrosoluble abrasive agents.

With one of the purposes of the cleansing composition being the removal of oil substances on the skin, the media for the compositions proposed to date do not contain fat bodies, or have only a relatively low concentration thereof, to avoid any addition of oils to the skin.

A number of products are commercially available which are directed to moisturizing the skin, thereby helping to maintain its youthful appearance and soft texture. While these products achieve varying degrees of success as moisturizing agents, research continues in an effort to develop more effective moisturizing agents.

Cells of the skin are constantly being generated during the natural cell renewal cycle of the skin. This cell renewal cycle involves the generation of new cells which rise through the epidermal layers of the skin until they reach the outer epidermal layer, or stratum corneum, where the skin cells die and eventually fall or slough off. Young skin renews its surface layers every two to three weeks, whereas mature skin may take twice as long to be renewed as compared to young skin. The longer the cell renewal process, the greater the loss of natural moisture on the skin's surface, thereby making the skin feel dry.

By accelerating the renewal of cells on the skin, the skin can be made to appear younger and fresher-looking. Many moisturizers currently available cause such acceleration by irritating the skin's surface to such a degree so as to cause sloughing off of stratum corneum cells. However, such irritation is not desired because of the potential damage to the skin.

The key to a more moisturized and, consequently, more youthful-looking skin is the proper conditioning of the skin. The proper "conditioning" of the skin requires, inter alia, the removal of dead skin cells from the surface of the skin.

It is known that cell renewal, i.e., eliminating old skin cells, encourages new skin cells. The epidermal cells are in a continuous state of regeneration and renewal. It has also been reported that the first signs of aging start to appear when a person is in his or her late 20's and early 30's. New epidermal cells are formed in the basal layer, the bottom layer of the epidermis. When they are first formed, they are round and "plump" (full of moisture). These cells travel through the four epidermal layers until they reach the surface or top layer, the stratum corneum. As they travel, they become older, flatter and drier-looking. By the time they reach the stratum corneum, the layer of skin that is seen, they are very flat and are ready to be shed or scraped off. As a person ages, cell turnover time, the transit time for which it takes new cells that are formed in the bottom or basal layer of the epidermis to travel through the various layers until they reach the top layer or stratum corneum becomes slower. It is documented that when a person is approximately twenty years old, the cells in the top layer of the epidermis will be sloughed off and replaced every two or three weeks. When that person is approximately eighty years old, the replacement can take up to twice as long. Since the epidermis is in a continuous state of self-replacement or turnover, with new cells being born in the basal layer to replace the old cells being shed from the stratum corneum, it follows that if the rate of cells in the stratum corneum that are being desquamated or shed is accelerated, the rate at which new cells are formed to replace them will also increase.

There are already available other procedures, both surgical and non-surgical means, by which cell renewal can be hastened to rejuvenate the skin so that the skin can retain moisture and have a more youthful, healthy, firmer and cleaner appearance. The reality is that none of these procedures are permanent. Because the cells are constantly being formed and surfacing to the stratum corneum, and must be shed at least every two or three weeks, the treatment, whatever the method, must be repeated. Moreover, none of the procedures are without some risk, either due to the techniques being employed or the varying expertise of physicians performing them. There is also the added risk and liability when the procedure requires the use of an anesthetic.

It is an object of the present invention to provide a novel skin exfoliant and cleansing composition and method which are not subject to the disadvantages noted above.

SUMMARY OF THE INVENTION

These and other objects are realized by the present invention, one embodiment of which comprises a skin cleansing and exfoliant composition comprising a mixture of d-alpha tocopheryl acetate (Vitamin E) homogenized in a pharmacologically acceptable oil phase and an emulsion or suspension of retinoic acid or a pharmacologically acceptable derivative thereof in a pharmacologically acceptable fluid adapted for application to human or non-human animal skin, the portion of the Vitamin E in the pharmacologically acceptable oil phase being sufficient to provide a concentration in the emulsion or suspension of from about 20% to about 40% by weight.

Another embodiment of the invention comprises a method for cleansing and exfoliating human or non-human animal skin by applying a skin-cleansing and -exfoliating effective amount of the above-described mixture to the skin, massaging the skin with the mixture for a time sufficient to cleanse and exfoliate the same, and thereafter immediately removing the mixture from the skin with exfoliated skin and material cleansed from the skin.

DETAILED DESCRIPTION OF THE INVENTION

The present invention is predicated on the discovery that the mixture of the above-described oil phase and retinoic acid or derivative thereof containing the emulsion or suspension, when applied to the skin, gives rise to unique exfoliating and cleansing actions not obtainable with other commercially available compositions or skin-treating procedures.

The suspension or emulsion component of the invention should contain from about 60% to about 80% by weight of retinoic acid or derivative thereof based on the weight of the emulsion. Although any pharmaceutically acceptable derivative of retinoic acid may be employed, it is preferred to utilize the higher fatty alcohol esters of retinoic acid, e.g., retinyl palmitate, etc.

The fluid mixture should contain from about 20% to about 40% by weight of homogenized Vitamin E (d-alpha tocopheryl acetate) based on the weight of the final composition. The Vitamin E component is preferably dissolved in an oil suitable for application to human skin or dispersed in an oil-water emulsion before admixture with the phase containing the retinoic acid or derivative thereof. Suitable such oils include sunflower oil, grapeseed oil, safflower oil, canola oil, tocopheryl acetate, sesame oil and emulsions or dispersions of these oils with water. The oil employed, of course, should be miscible and compatible with the oil base employed to prepare the retinoic acid or derivative emulsion.

Suitable oils for inclusion in the composition of the invention include any suitable vegetable oil (containing Vitamin E) such as corn oil, canola oil, etc., or oil derived from fruit such as grapeseed oil. The most preferred oils, however, which exhibit significantly better exfoliant activity, are sunflower oil and grapeseed oil, containing Vitamin E.

After massaging into the skin for a time sufficient to loosen dead skin cells and debris, the composition is immediately washed off with tepid tap water. A massage period of 15 to 30 minutes per area of skin treated will achieve very beneficial results, i.e., the removal of a large amount of dead skin, dirt, debris, etc. A massage period extended up to 2 hours per area of skin treated applying multiple layers of the mixture of the invention will result in the removal of an extraordinary amount of dead skin, dirt, debris, etc. A massage period of from about 15 minutes up to about 2 hours is generally sufficient to remove all dead skin, dirt, debris, etc.

The suspension or emulsion of retinoic acid or derivative thereof may contain any suitable cosmetic or skin-enhancing ingredient, preparation, emulsifying or suspending agent, etc., commonly employed in commercial moisturizing compositions.

The formulation of the invention is non-irritating to the skin and is completely non-toxic.

The retinoic acid or derivative thereof is preferably suspended or emulsified in any suitable carrier base compatible with the oil phase of the composition of the invention and suitable for application to human skin. Suitable such materials are outlined in "Encyclopedia of Chemical Technology," 3d ed., and Remington's Pharmaceutical Sciences, 4th ed. (1970), the contents of both of which are incorporated herein by reference. Preferred are the well known emollients and skin moisturizing compositions which include, for example, 2-ethyl hexyl oxystearate. Particularly useful emollients which provide skin conditioning are glycerol, hexanetriol, butanetriol, lactic acid and its salts, urea, pyrrolidone carboxylic acid and its salts, amino acids, guanidine, diglycerol and triglycerol. Other ingredients conventionally used in topical preparations such as water-soluble alcohols, glycols, surfactants, perfumes, preservatives, hydrophilic polymers, emulsifiers, natural and synthetic oils, lanolin, fatty alcohols, etc., may be added to the compositions. Hydrophilic polymers may be added to increase the viscosity or gel the composition and include such materials as hydrophilic acrylic polymers, polyvinyl alcohol, gelatin, hydroxyethyl cellulose, carboxymethyl cellulose, gum tragacanth, gum karaya, gum arabic and other thickening agents known to those skilled in the pharmaceutical formulation art.

It is preferred to formulate the packaged products such that the total concentration of oil phase in the admixed composition is about 20% by weight. This amount ensures obtention of the most desirable result, i.e., rapid and complete exfoliation of dead skin and more moisturized skin. Although higher and lower concentrations of oil phase may be employed, the results obtained will be inferior to those produced using 20% to 40% by weight of oil. Thus, using less than 20% oil, the skin will feel less moisturized, whereas employing more than about 40% oil will result in the skin feeling excessively oily.

The invention is illustrated by the following non-limiting example.

EXAMPLE

The suspension of retinyl palmitate described above was mixed with both sunflower oil and grapeseed oil, containing homogenized d-alpha tocopheryl acetate (Vitamin E) immediately prior to use such that the concentration of oil in the composition was 20% by weight. The face and body of a human subject was covered with the mixture and a large amount of skin debris, found to consist largely of dead skin cells, was discharged/exfoliated from the skin after only one application and massage of the skin surface for only 2-5 minutes. During the massage process, of up to 15 minutes, additional quantities of the mixture were layered upon the skin surface, resulting in even greater amounts of debris being discharged. The mixture was removed with tepid tap water. The treated skin felt smooth, soft, comfortable and moisturized. Repeating the process 2 times daily for 3 days led to the exposure of the lowermost layer of new skin. There was no irritation or other toxic reaction to the application of the mixture.

The result was that the subject's skin was much less wrinkled than before treatment and the skin retained a more youthful appearance for three to four weeks, at which time the process was repeated.

To demonstrate the unobvious synergistic action of d-alpha tocopheryl acetate (Vitamin E) and retinoic acid (or derivative) as a skin cleanser and exfoliant, a large number of commercially available products, used as topical applications only, and containing either Vitamin E or retinyl palmitate, or both, were tested independently, via deep massage, on the skin of a human subject. None of these products produced any exfoliation of skin debris, even after several hours of massage application.

I claim:

1. A skin cleansing and exfoliant composition comprising a mixture of:
   (1) an oil phase of d-tocopheryl acetate (Vitamin E) homogenized in a pharmacologically acceptable oil; and
   (2) an emulsion or suspension of retinoic acid or a ester of retinoic acid in a pharmacologically acceptable fluid adapted for application to human or non-human animal skin, the concentration of said retinoic acid or derivative thereof in said emulsion or suspension being in the range of from about 60% to about 80% by weight, said portion of the d-alpha tocopheryl acetate (Vitamin E) in the oil phase being sufficient to provide a concentration of from about 20% to about 40% by weight of the composition.

2. The composition of claim 1 wherein said retinoic acid derivative is an ester of retinoic acid and a fatty alcohol.

3. The composition of claim 2 wherein said ester is retinyl palmitate.

4. The composition of claim 1 wherein said oil is a vegetable oil, containing Vitamin E.

5. The composition of claim 1 wherein said oil is sunflower oil, containing Vitamin E.

6. The composition of claim 1 wherein said oil is derived from fruit, containing Vitamin E.

7. The composition of claim 1 wherein said oil is grapeseed oil, containing Vitamin E.

8. The composition of claim 1 wherein said portion of oil phase is sufficient to provide a concentration in said emulsion or suspension of about 20% by weight.

9. The composition of claim 1 wherein said portion of oil phase is sufficient to provide a concentration in said emulsion or suspension of about 40% by weight.

10. The composition of claim 1 wherein the concentration of said retinoic acid or derivative thereof in said emulsion or suspension is about 60% by weight.

11. The composition of claim 1 wherein the concentration of said retinoic acid or derivative thereof in said emulsion or suspension is about 80% by weight.

12. A method for cleansing and exfoliating human or non-human animal skin, the method comprising the steps of:
    massaging said skin for from 15 minutes up to two hours to cleanse and exfoliate the skin with a composition comprising a mixture of:
    (1) an oil phase of d-tocopheryl acetate (Vitamin E) homogenized in a pharmacologically acceptable oil; and
    (2) an emulsion or suspension of retinoic acid or a an ester of retinoic acid in a pharmacologically acceptable fluid adapted for application to human or non-human animal skin, the concentration of said retinoic acid or derivative thereof in said emulsion or suspension being in the range of from about 60% to about 80% by weight, said portion of the d-alpha tocopheryl acetate (Vitamin E) in the oil phase being sufficient to provide a concentration of from about 20% to about 40% by weight of the composition, and thereafter removing said mixture from said skin.

* * * * *